(12) United States Patent
Leblans et al.

(10) Patent No.: US 6,504,169 B1
(45) Date of Patent: *Jan. 7, 2003

(54) METHOD FOR READING A RADIATION IMAGE THAT HAS BEEN STORED IN A PHOTOSTIMULABLE SCREEN

(75) Inventors: Paul Leblans, Kontich (BE); Luc Struye, Mortsel (BE)

(73) Assignee: Agfa-Gevaert, Mortsel (BE)

( * ) Notice: Subject to any disclaimer, the term of this patent is extended or adjusted under 35 U.S.C. 154(b) by 4 days.

This patent is subject to a terminal disclaimer.

(21) Appl. No.: 09/595,183

(22) Filed: Jun. 16, 2000

Related U.S. Application Data

(60) Provisional application No. 60/142,276, filed on Jul. 2, 1999, and provisional application No. 60/159,004, filed on Oct. 8, 1999.

(51) Int. Cl.[7] .............................. G01N 23/04; A61B 6/00
(52) U.S. Cl. ........................................ 250/588; 250/582
(58) Field of Search ................................ 250/581, 582, 250/588

(56) References Cited

U.S. PATENT DOCUMENTS

| | | | |
|---|---|---|---|
| 3,859,527 A | | 1/1975 | Luckey |
| 4,835,386 A | * | 5/1989 | Shimura ............... 250/588 |
| 4,883,961 A | * | 11/1989 | Arakawa ............... 250/588 |
| 5,028,509 A | | 7/1991 | Shimada et al. |
| 5,072,119 A | * | 12/1991 | Yamaguchi ............ 250/588 |
| 5,434,431 A | * | 7/1995 | Verbeke et al. ........ 250/588 |

FOREIGN PATENT DOCUMENTS

| | | | | |
|---|---|---|---|---|
| EP | 0174875 | * | 3/1986 | ........... C09K/11/61 |
| EP | 0 174 875 | | 6/1990 | |

OTHER PUBLICATIONS

Sristava, AM, TJ Sommerer: Fluorescent Lamp Phosphors, The Electrochemical Society Interface, Summer 1998, p. 28.

* cited by examiner

Primary Examiner—Georgia Epps
Assistant Examiner—Alicia M Harrington
(74) Attorney, Agent, or Firm—John A. Merecki; Hoffman, Warnick & D'Alessandro

(57) ABSTRACT

A radiation image read out method and apparatus including stimulating a divalent europium activated cesium halide phosphor screen wherein the halide is at least one of chloride and bromide, that has been exposed to a radiation image, detecting light emitted by the phosphor screen upon stimulation, and erasing the phosphor screen by exposing it to erasing light emitted by an erasing light source assembly having an electrical erasing energy not greater than $S_{max} \times 1$ Joule wherein $S_{max}$ is the maximum surface area of the stimulable phosphor screen read out in a read out apparatus.

4 Claims, 5 Drawing Sheets

METHOD FOR READING A RADIATION IMAGE THAT HAS BEEN STORED IN A PHOTOSTIMULABLE SCREEN

This application claims the benefit of copending U.S. Appln. No. 60/142,276 filed Jul. 2, 1999 and Appln. No. 60/159,004 filed Oct. 8, 1999.

FIELD OF THE INVENTION

The present invention relates to a method and a system of reading a radiation image that has been stored in a photostimulable phosphor screen. More particularly the invention relates to the re-use of the photostimulable phosphor screen.

BACKGROUND OF THE INVENTION

Radiation image recording systems wherein a radiation image is recorded on a photostimulable phosphor screen by exposing said screen to image-wise modulated penetrating radiation are widely used nowadays.

The recorded image is reproduced by stimulating the exposed photostimulable phosphor screen by means of stimulating radiation and by detecting the light that is emitted by the phosphor screen upon stimulation and converting the detected light into an electrical signal representation of the radiation image.

In such a system it is preferred, in view of economy, that the stimulable phosphor screen can be used in many imaging cycles.

The reuse of the stimulable phosphor screen is possible when the previously stored radiation image is erased to a sufficient extent.

When reading out an image by stimulating a phosphor screen that has been exposed to penetrating radiation, less than 90% of the stored energy is released. Thus there arises a problem that, upon reuse, part of the radiation image is still stored in the phosphor screen and can appear in the subsequent image as a so-called ghost image.

In general medical radiography, images are made with widely differing X-ray doses.

To make images of extremities, like e.g. fingers, doses are used of the order of 1 mR. On the other hand, images of internal organs, like the stomach are made with X-ray doses that may be as high as 300 mR.

To avoid ghosting, when making a 1 mR image immediately after a 300 mR image, the signal of the first image must be reduced by more than a factor of 300.

As a matter of fact, a dynamic range is desired in the second image of at least 100. This implies that the signal created by the first irradiation must be reduced by a factor of at least $3.10^4$, which is equivalent to requiring an erasure depth of $1/(3.10^4)=3.3.10^{-5}$.

According to U.S. Pat. No. 3,859,527 (column 4, lines 5–7) the phosphor can be reduced to neutral state by actions like a uniform illumination, irradiation or heating.

In commercial systems, the phosphor screen is erased by illumination with visible light. Incandescent lamps are commonly used because they are cheap, high power light sources.

High power is needed, because in order to guarantee a high through-put scanning system, the phosphor screen must be erased in a short time.

High power lamps, however, generate a lot of heat, which may destabilise the scanner to read out the storage phosphor screens. The size of the read out apparatus has to be rather large in order to enable removal of the heat generated by a powerful erasure unit which is required in order to have a high throughput.

In order to develop a reliable and compact storage phosphor screen digital radiography system it is important to reduce the power consumed by the erasure unit. This was not possible, however, without affecting the system's throughput in a negative way.

OBJECTS OF THE INVENTION

It is an object of the present invention to provide a method and a system for reading a radiation image that has been stored in a photostimulable phosphor screen wherein the screen is erased in between successive recordings to an adequate extent so as to permit re-use of the screen.

It is a further object of the present invention to provide such a system that is compact and has at the same time a high throughput.

Further objects will become apparent from the description given below.

SUMMARY OF THE INVENTION

The above mentioned objects are realised by a method of reading a radiation image that has been stored in a photostimulable phosphor screen having a surface area that is not greater than $S_{max}$ comprising the steps of (1) stimulating said phosphor screen by means of stimulating radiation, (2) detecting light emitted by the phosphor screen upon stimulation and converting the detected light into a signal representation of said radiation image, (3) erasing said phosphor screen by exposing it to erasing light, characterised in that (4) said photostimulable phosphor screen comprises a divalent europium activated cesium halide phosphor wherein said halide is at least one of chloride and bromide and said erasing light is emitted by an erasing light source assembly emitting in the wavelength range of 300 nm to 1500 nm and having an electrical power not greater than $S_{max} \times 1$ J.

The terms 'an erasing light source assembly' refer to either a single light source or a group of more than one erasing light source. In the latter case the electrical power which is specified is the electrical power of the total assembly.

According to the invention the wavelength of the erasing light source(s) is within the range of 300 nm to 1500 nm. A wavelength range from 500 nm to 800 nm is preferred because a divalent europium activated cesium halide phosphor is most efficiently erased with light within this wavelength range.

Another aspect of the present invention relates to a radiation image read out apparatus for reading a radiation image that has been stored in photostimulable phosphor screen having a surface area not greater than $S_{max}$, having
 a source of stimulating radiation arranged for emitting stimulating light and directing said light onto a photostimulable phosphor screen,
 a transducer for converting light emitted by said phosphor screen upon stimulation into an electrical signal,
 an erasing unit for erasing said photostimulable phosphor screen after having been stimulated, characterised in that
 said photostimulable phosphor screen comprises a divalent europium activated cesium halide phosphor wherein said halide is at least one of chloride and bromide, and said erasing unit comprising at least one erasing light source, the total electrical power of the erasing light source(s) of the erasing unit being smaller than $S_{max} \times 1$ J.

Still another aspect relates to a re-usable radiation detector comprising a photostimulable phosphor screen, at least one source of stimulating light arranged for stimulating said phosphor screen, an array of transducer elements arranged for capturing light emitted by the phoshor screen upon stimulation and for converting said light into an electrical signal representation, an erasing unit comprising at least one erasing light source, means for transporting the phosphor screen and an assembly of stimulating light source(s), said array of transducer elements and said erasing unit relative to the each other, an enclosure enclosing said photostimulable phosphor screen, said assembly of stimulating light source, erasing light source, said array of transducer elements, said transporting means, interfacing means for communicating said electrical signal representation to an external signal processing device.

Specific features for preferred embodiments of the invention are disclosed in the dependent claims.

The objects of the present invention are realised in a read out method and apparatus and detector according to the present invention by using a phosphor with a very good erasability combined with an erasure unit with low electrical power.

The inventors have found that the use of an erasing light source of a low power type is adequate in a system wherein a radiation image is temporarily stored in a divalent europium activated cesium halide phosphor without there being any need for the phosphor screen to remain for an extended period of time in the erasing unit. Consequentially the fact that a low power erasing light source is used has no negative influence on the throughput of the system.

Furthermore, since a low power erasing light source has a low heat dissipation, no particular precautions (such as the provision of fans or the like) have to be taken to dissipate the heat generated by the erasing light source. Consequentially the read out system can be made very compact and still remain very reliable.

In this document the term "radiation" has to be understood as any penetrating radiation and includes irradiation originating from a radioisotope (e.g. Co60, Ir192, Se75, etc.), radiation created by an X-ray generator of any type, radiation and high energy particles created by a high energy radiation generator (e.g. Betatron), radiation from a sample labeled with a radioisotope as is the case in e.g. autoradiography.

The present invention as well as specific and/or preferred embodiments hereof will be explained in the detailed description given below. Particular aspects will be illustrated by the drawings enumerated hereinafter.

DETAILED DESCRIPTION OF THE INVENTION

Figure 1:
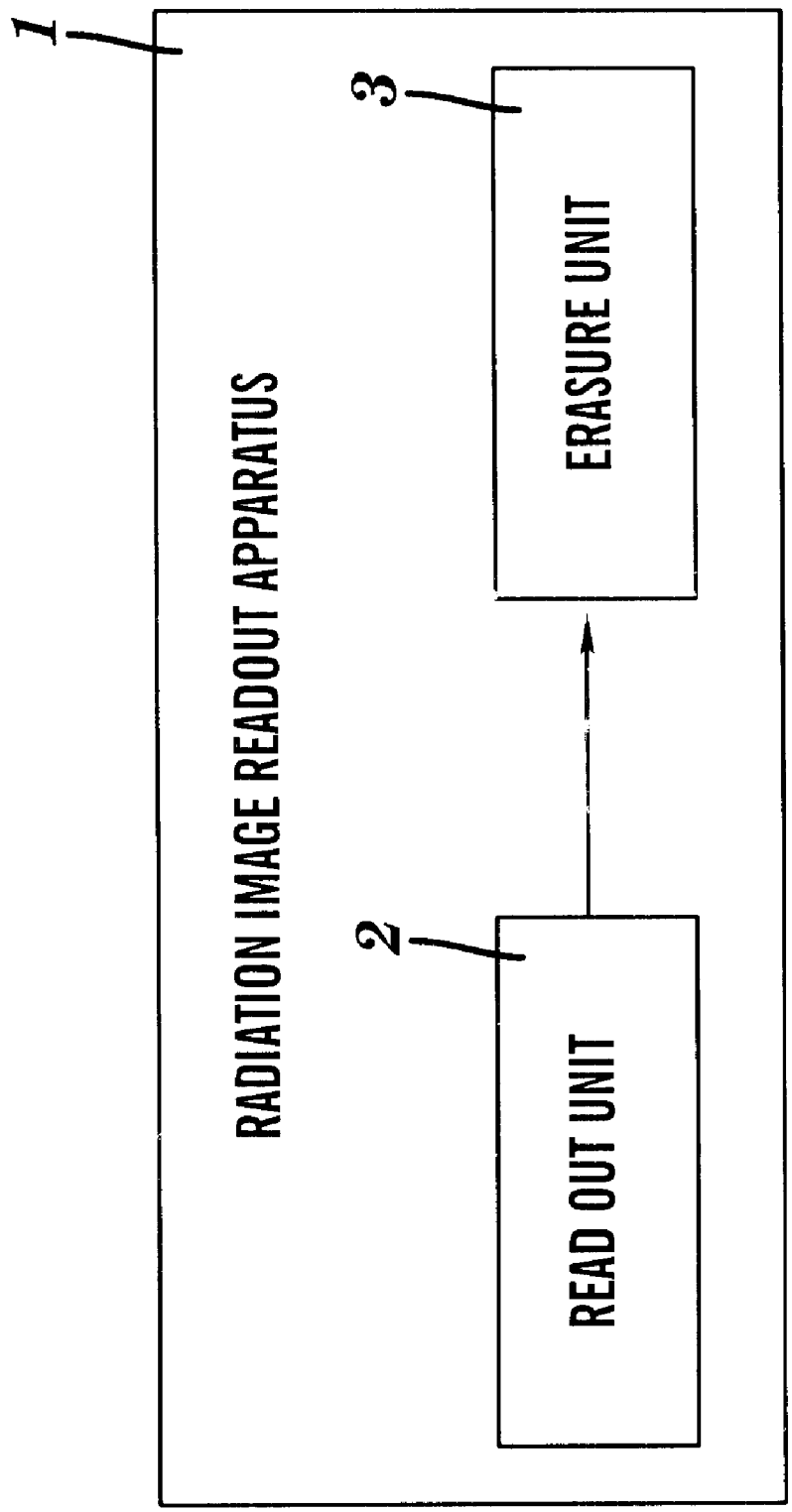
FIG. 1 is a block diagram representing the main components of an image read out apparatus comprising an erasure unit.

A radiation image read out device (1) according to the present invention is schematically shown in FIG. 1. The device generally comprises a image read out unit (2) and an erasure unit (3).

The read out and erasure units can be implemented as separate units or can be incorporated into a single unit.

Figure 2:
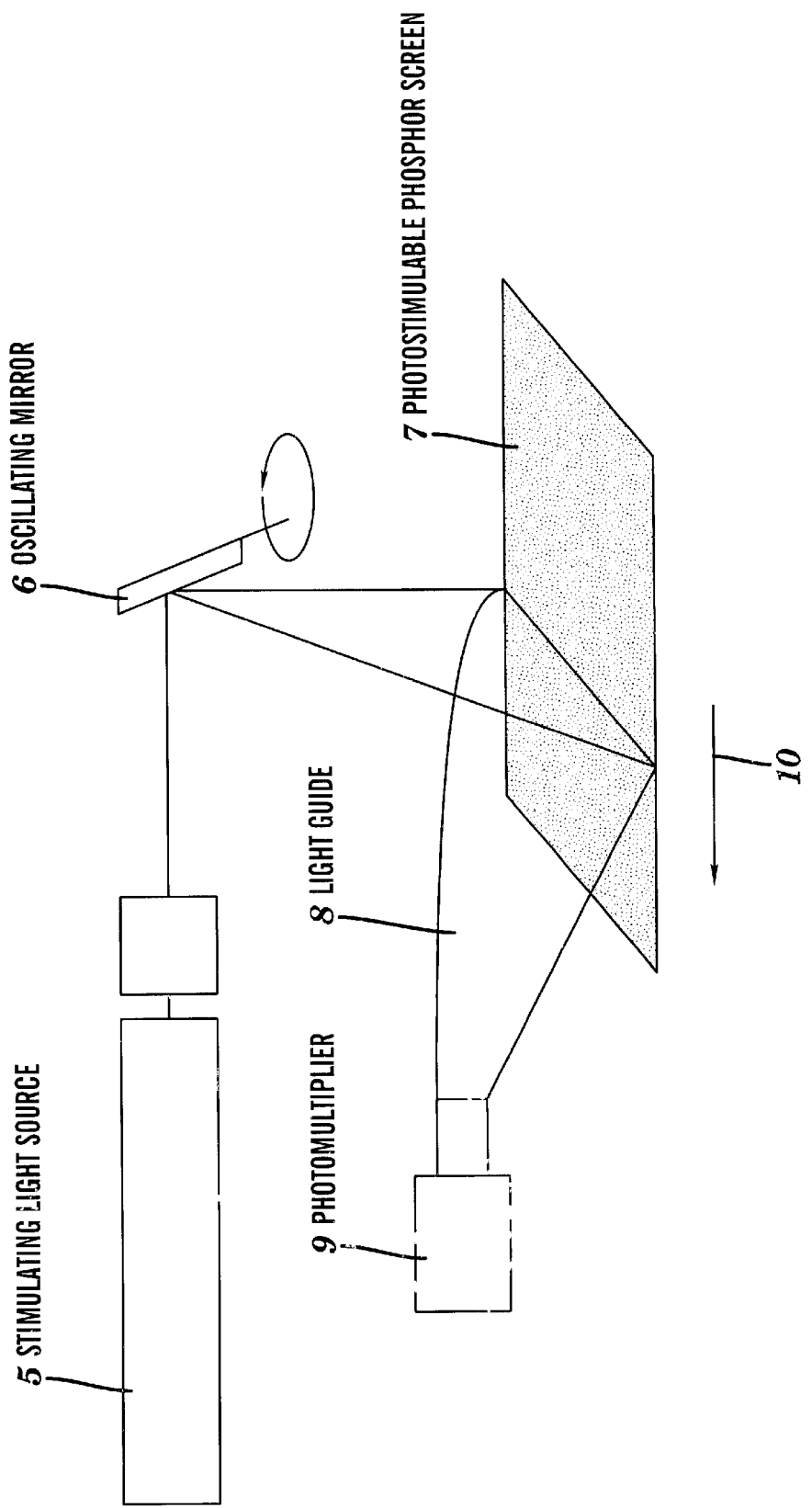
FIG. 2 shows an embodiment of a photostimulable phosphor read out unit of the flying spot type.

A first embodiment of an image read out unit is of the flying spot scanner type, this embodiment is shown in greater detail in FIG. 2.

The read out unit comprises a source of stimulating radiation (5), more particulary a HeNe laser emitting light at 633 nm.

The unit further comprises an oscillating mirror (6) for deflecting light emitted by the stimulating laser source onto the photostimulable phosphor screen (7) into the scan direction, a light guide (8) for guiding light emitted by the photostimulable phosphor screen upon stimulation onto a photomultiplier (9).

The read out unit further comprises means for transporting (not shown) the photostimulable phosphor screen into the sub-scan direction indicated by arrow (10).

It will be clear that various alternatives for the components of the apparatus may be envisaged, e.g. the HeNe laser can be replaced by a diode laser emitting at 630 nm, the oscillating mirror can be replaced by a multi-facet mirror etc.

A read out unit of the flying spot type is generally combined with an erasure unit that is optically separated from the read out unit so that there is no interference between read out and erasure. The photostimulable phosphor screen is transported through the read unit into the erasure unit. An image line which has been read out is subsequently erased. The erasure can be performed by a part-by-part (e.g. line-by-line) erasing illumination of the screen or by means of an overall erasing illumination.

A read out apparatus of the above-described kind is commonly used for read out of phosphor screens of a variety of dimensions which are selected for different kinds of applications. However, the dimensions of the read out apparatus and the available possibilities for adjustment of optical and mechanical components imply a maximum format of the screen that can be read out in an apparatus. This maximum format is denoted as $S_{max}$.

In accordance with the present invention the erasure section comprises at least one erasing light source emitting in the range of 300 to 1500 nm. The total electrical power of the erasing unit is not more than 1 Joule multiplied by $S_{max}$ wherein $S_{max}$ is the surface of the largest photostimulable phosphor screen that can be read out in the envisioned read out apparatus (in $cm^2$).

The wavelength range is selected so as to be optimally matched to the characteristics of the europium activated cesium halide phosphor. The europium activated cesium halide phosphor is most efficiently erased with erasure light within the wavelength range of 500 to 800 nm.

In the described embodiment an elongate flash lamp such as a Xenon or Krypton flash lamp, is preferably used. This kind of flash lamps emits in the range of 500 to 800 nm, and is thus appropriate for erasure of the europium activated cesium halide phosphor. Furthermore it is a low power light source and it has an appropriate shape for integration in a compact read out unit.

Alternatives such as a laser or a quartz halogen lamp could be used. However, the performance of the flash lamp is much better than that of the quartz halogen lamp.

Figure 3:
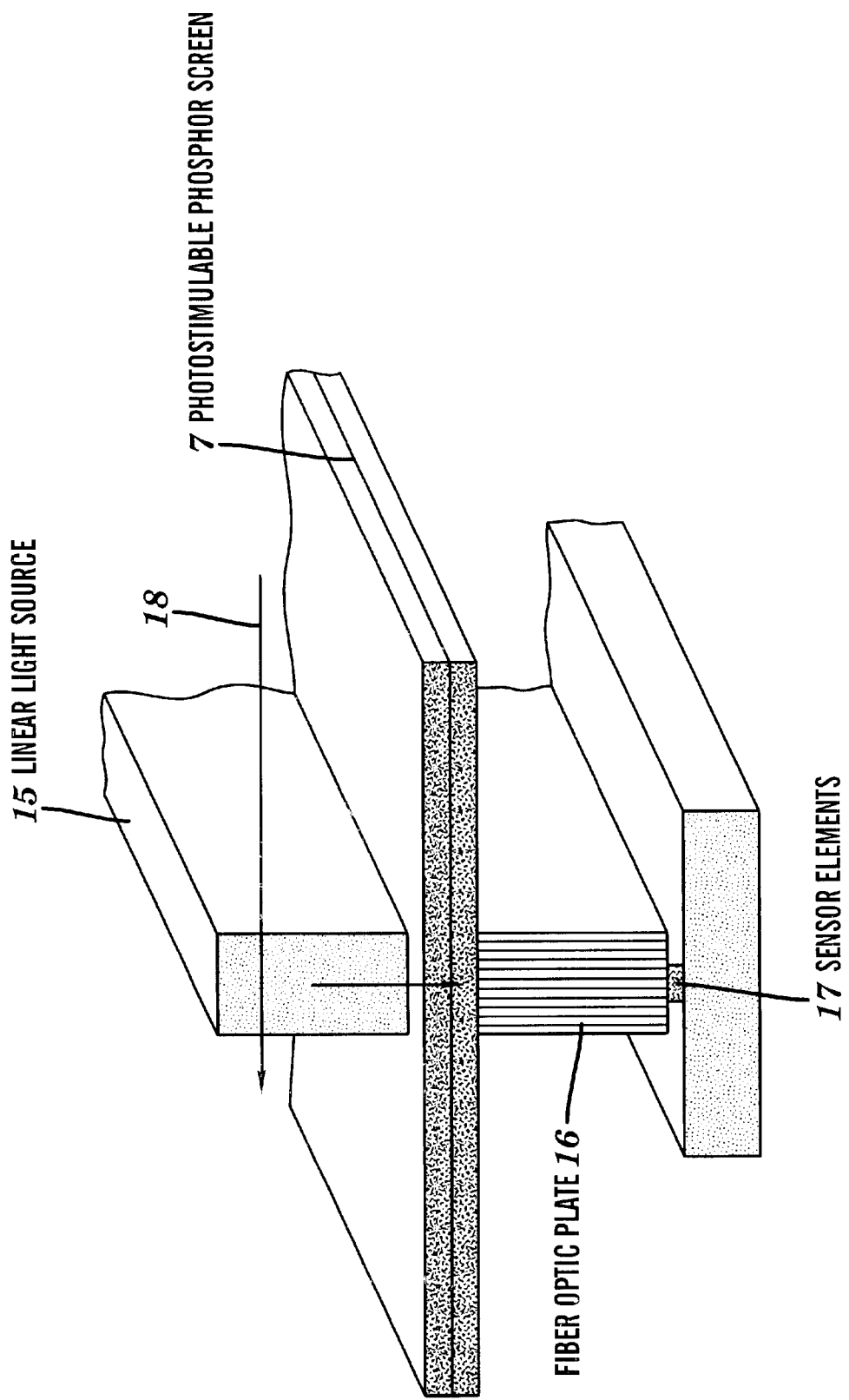
FIG. 3 shows a second embodiment of photostimulable phosphor read out unit, referred to as scan-head type, FIG. 4 schematically shows the position of the stimulating light source and the erasing light source in the embodiment of FIG. 3.

A second embodiment of a read out unit, referred to as scan-head type read out unit type is shown in FIG. 3.

The described scan-head type differs from the conventional flying spot type in that in the scan-head type the image read out is line-wise whereas in the conventional flying spot type read out unit the reading is performed in a point-by-point fashion.

In one embodiment the read out unit comprises a linear light source (15) for emitting stimulating light onto the photostimulable phospor screen.

This linear light source comprises 4096 individual laser diodes arranged in a row. This light source provides simultaneous illumination of all pixels of a single line of the photostimulable phosphor screen.

The read out unit further comprises a fiber optic plate (16) for directing light emitted by the phosphor screen upon stimulation onto a linear array of sensor elements (17), more particulary charge coupled devices. The fiber optic plate (16) comprises a number of parallel mounted light guiding fibers arranged so as to guide the light emitted by each individual element of an illuminated line onto a sensor element.

Alternatively the fiber optic plate can be replaced by an arrangement of selfoc lenses or microlenses. A light guide member might even be avoided.

Alternatives may also be envisaged for the linear light source. This linear light source can be replaced by a 'flying spot' light source. The light emitted by this light source is then deflected by a rotatable polygon mirror onto a scan line on the phosphor screen. In this way one point of this line at the time is illuminated.

In the embodiment shown in FIG. 3 the linear light source is arranged on one side of the phosphor screen, the fiber optic plate and the linear array of sensor elements being arranged on the opposite side. Either of these elements extends in the direction of a scan line.

During read out, the phosphor screen on the one hand and the assembly of fiber optic plate and sensor array on the other hand are displaced relative to each other in the direction of arrow (18).

In still another embodiment which is not shown the array of stimulating light sources, the fiber optic plate and the sensor array are arranged at the same side of the photostimulable phosphor screen.

After read out the photostimulable phosphor screen is erased so that the energy remaining in the screen after read out is released and so that the screen is in a condition for re-use.

In the type of read out apparatus wherein stimulation is performed by means of light emitted by a linear light source extending parallel to a scan line on the stimulable phosphor screen, the erasure unit preferably forms part of the read out unit.

Figure 4:
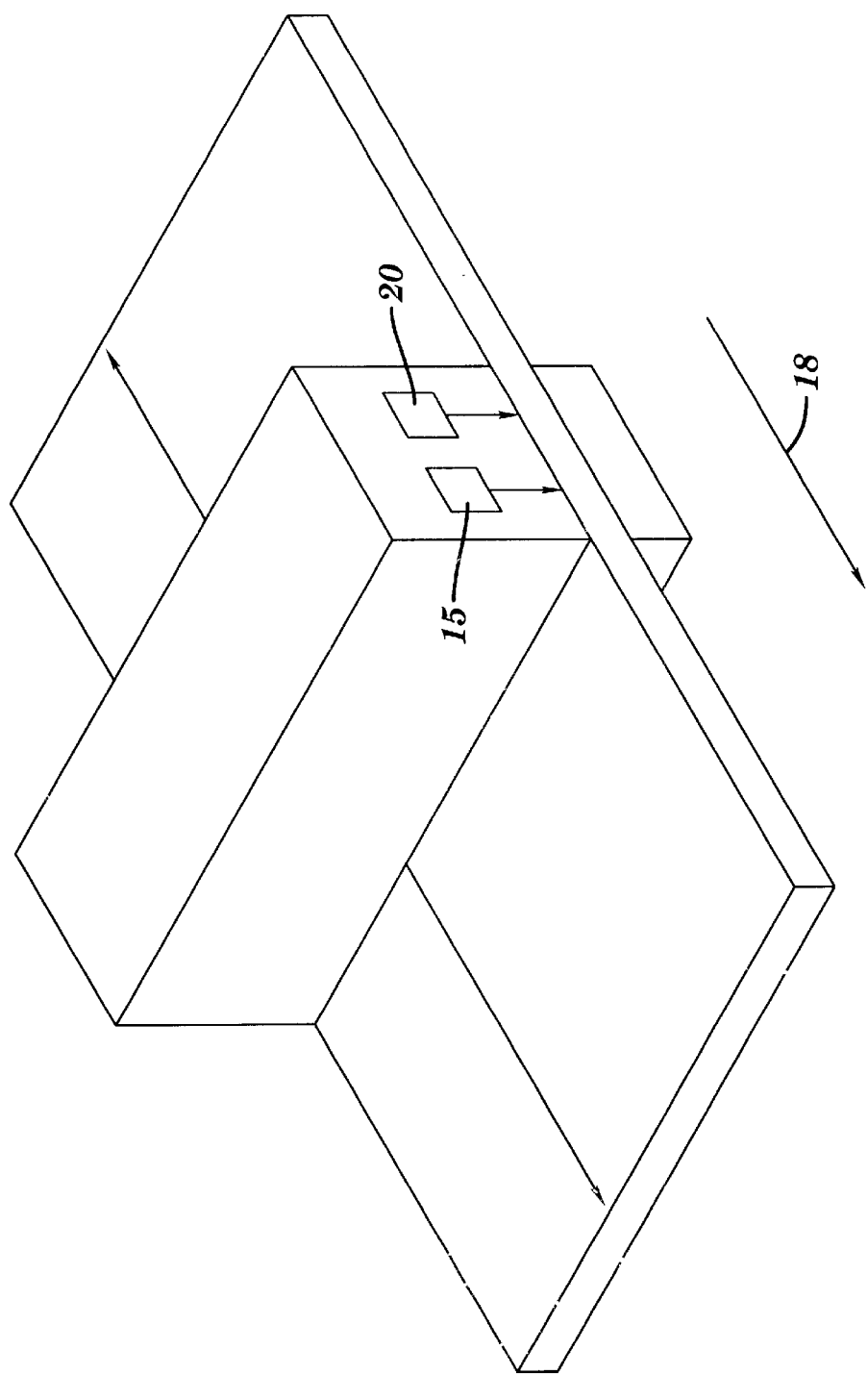

In the embodiment shown in FIG. 3, the erasing light source (20) is part of an assembly comprising the stimulating light source and the light guiding and light detecting means. The position of the stimulating light source and of the erasing light source is shown schematically in FIG. 4.

According to the present invention the erasing section comprises an erasing light source emitting in the range of 300 nm to 1500 nm and having an electrical power of not more than $1 \text{ J} \times S_{max}$.

In the described embodiment an elongate flash lamp such as a Xenon or Krypton flash lamp, is preferably used. This kind of flash lamps emits in the range of 500 to 800 nm, and is thus appropriate for erasure of the europium activated cesium halide phosphor. Furthermore it is a low power light source which has an appropriate shape for integration in a compact read out unit.

Alternatives such as a laser or a quartz halogen lamp could be used. However, the performance of the flash lamp is much better than that of the quartz halogen lamp.

The erasing light source is arranged parallel to the linear array of stimulating light sources. The erasing light source is transported past the image that is read at the same transportation speed in between 30 mm/sec and 250 mm/sec. In this way the erasing light source illuminates a line of the image after it has been submitted to read out.

Figure 5:
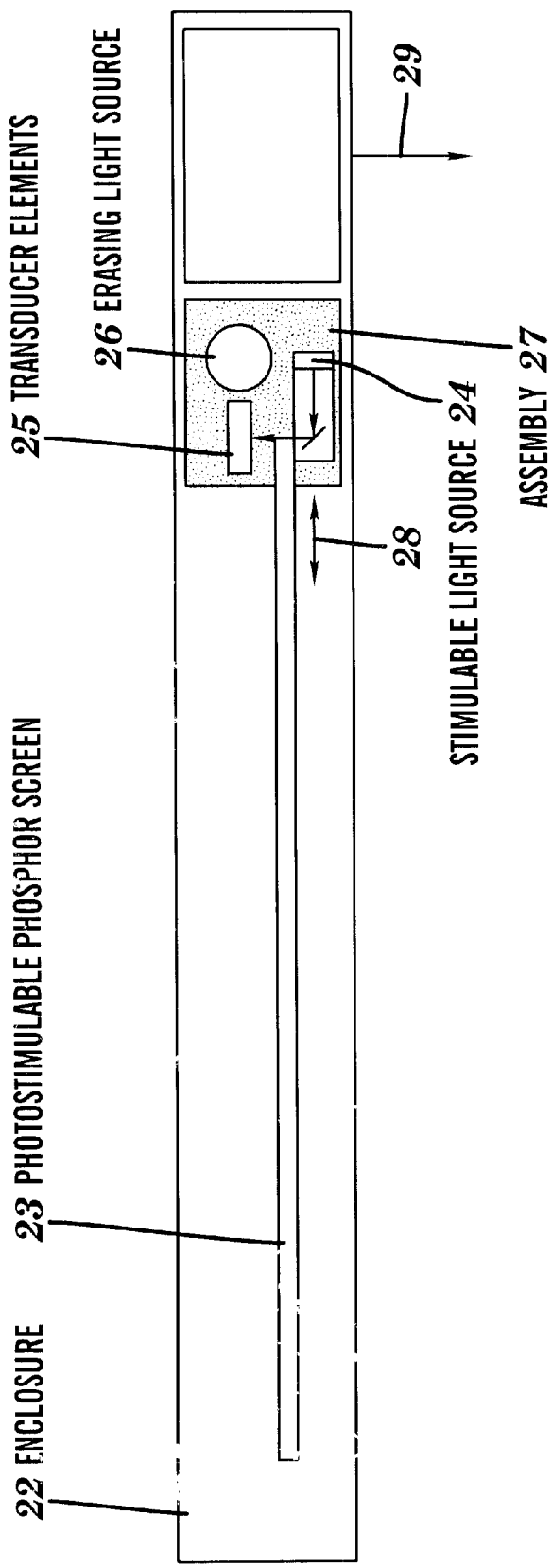
FIG. 5 shows a radiation detector according to the present invention.

Another aspect of the present invention relates to a re-usable radiation detector. This type of detector is shown in FIG. 5.

The detector comprises an enclosure (22).

Within the enclosure a photostimulable phosphor screen (23) is positioned. This screen preferably comprises a divalent cesium halide phoshor, wherein said halide is at least one of chloride and bromide.

The enclosure further comprises a source of stimulating light (24) arranged for stimulating said phosphor screen and an array of transducer elements (25) for capturing light emitted by the phoshor upon stimulation and for converting said light into an electrical signal representation. In the illustrated embodiment the source of stimulating light is a linear light source and the array of transducer elements is also a linear array. This embodiment can be made very compact and provides fast read out.

The enclosure further comprises a linear erasing light source (26) arranged substantially parallel to the stimulating light source.

The enclosure still further comprises means (not shown) for transporting the assembly (27) of stimulating light source, erasing light source and array of transducer elements relative to the phosphor screen in a so-called sub-scan direction, indicated by arrow (28).

Means (29) are further provided for communicating the electrical signal representation output by the array of transducer elements to an external signal processing device.

In this re-usable radiation detector the phosphor screen remains inside the enclosure during irradiation, read out and erasure.

In this embodiment the stimulating light source and the array of transducer elements are arranged on opposite sides of the phosphor screen.

In alternative embodiment these items may be arranged on the same side of the phosphor screen.

The stimulable phosphor screen in the several embodiments of the present invention comprises a divalent europium activated cesium halide phosphor. Such a phosphor is known in the art and has for example been disclosed in EP-A-174 875 (and U.S. Pat. No. 5,028,509). The phosphor is especially well suited for manufacturing 'binderless' phosphor screens. Binderless phosphor screens provide optimal sharpness.

It is advantageous however to use a CsX:Eu phosphor wherein X represents a halide selected from the group consisting of Br and Cl, which is obtained by the following method:

mixing CsX with between $10^{-3}$ and 5 mol % of a Europium compound selected from the group consisting of $EuX'_2$, $EuX'_3$ and $EuOX'$, X' being a member selected from the group consisting of F, Cl, Br and I, firing the mixture at a temperature above 450° C.

cooling said mixture and recovering the CsX:Eu phosphor.

A phosphor that has been obtained as a result of the above method of preparation has an increased conversion efficiency compared to the state of the art divalent europium activated cesium halide phosphor. The phosphor can be stimulated by means of a lower amount of stimulation energy.

A photostimulable phosphor screen using such a phosphor is preferably obtained by the method of preparing said CsX:Eu phosphor by firing a mixture of said CsX with between 10-3 and 5 mol % of an Europium compound selected from the group consisting of $EuX'_2$, $EuX'_3$ and $EuOX'$, X' being a halide selected from the group consisting of F, Cl, Br and I and applying said phosphor on a substrate by a method selected from the group consisting of physical vapor deposition, thermal vapor deposition,, chemical vapor deposition, radio frequency deposition and pulsed laser deposition.

This method of preparation is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

Alternatively a phosphor screen containing a CsX:Eu stimulable phosphor, wherein X represents a halide selected from the group consisting of Br and Cl can also be manufactured by performing the steps of:

bringing multiple containers of said CsX and an Europium compound selected from the group consisting of $EuX'_2$, $EuX'_3$ and $EuOX'$, X' being a halide selected from the group consisting of F, Cl, Br and I in condition for vapor deposition and depositing, by a method selected from the group consisting of physical vapor deposition, thermal vapor deposition,, chemical vapor deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

This method of preparation is advantageous because it likewise allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

The above-described specific phosphors as well as their methods of preparation have been disclosed in US provisional applications Nos. 60/159,004 and 60/142,276 which are incorporated herein by reference.

Measurements of Erasability

The erasability of a CsBr:Eu screen was measured in comparison to a commercial MD-10 (trade name of Agfa-Gevaert N.V.) BaFBr:Eu screen of Agfa-Gevaert N.V.

Sample Preparation

The CsBr:Eu screen was produced in the following way:

A CsBr:Eu sample screen was made via thermal vapour deposition of CsBr and the EuOBr. To this aim, CsBr was mixed with EuOBr and placed in a container in a vacuum deposition chamber. The phosphor was deposited on a glass disk with a thickness of 1.5 mm and a diameter of 40 mm. The distance between the container and the substrate was 10 cm. During evaporation, the substrate was rotated at 12 rpm.

The substrate temperature was ca. 200° C. at the start of the evaporation process.

The container was heated to a temperature of 750° C.

Before the start of the evaporation, the chamber was evacuated to a pressure of $4.10^{-5}$ mbar. During the evaporation process, Ar was introduced in the chamber and the Ar gas pressure was $1.6 \cdot 10^{-2}$ mbar.

The resulting screen had a thickness of 850 m.

The Eu-concentration in the evaporated screen was measured with X-ray fluorescence. At the substrate side, the phosphor contained 400 ppm of Eu and at the surface side 800 ppm.

Measurement Procedure

In a first measurement, both screens were homogeneously irradiated with a dose of ca. 50 mR at 80 kVp.

The screens were read out in a flying spot scanner. The scanning light source was a 30 mW diode laser emitting at 690 nm. A 4 mm Hoya BG-39 (trade name) filter was used to separate the stimulation light from the light emiited by the phosphor screen. The scan-average levels (SAL) were determined as the average signal produced by the screens in the photomultiplier tube. The results of this measurement was a SALL value for the CsBr:Eu2+ screen and a SAL1 value for the MD-10 screen (Table 1).

In a second measurement, the MD-10 screen was homogeneously irradiated with a dose of ca. 44 R, also at 80 kVp.

Next, the screen was erased with a 500 W (electrical power) quartz-halogen lamp for 1 s. The light intensity at the screen position was measured using a photometer and was 12 mW/cm$^2$.

After erasure, the screen was read out with the above-described scanner, and the SAL was measured. This measurement yielded the SAL2 value for the MD-10 screen (Table 1).

Erasure depth, defined as the SAL after erasure divided by the SAL prior to erasure was calculated using the equation:

$$Ed=SAL2\times 50/(SAL1\times 44,000) \qquad (1),$$

where the factor 50/44,000 corrects for the difference in dose in the measurements 1 and 2. (Different doses were selected in order to enable image detection in all cases without having to adapt the sensitivity settings of the photomultiplier).

In a third measurement, the CsBr:Eu2+ screen was homogeneously irradiated with a dose of ca. 166 R, also at 80 kVp.

Next, the screen was erased with the 500 Watt quartz-halogen lamp for 1 s. The light intensity on the screen was, again, 12 mW/cm$^2$.

After erasure, the screen was read out with the above-described scanner, and the SAL was determined. This measurement yielded the SAL3 value for the CsBr:Eu$^{2+}$ screen (Table 1).

Erasure depth, defined as the SAL after erasure divided by the SAL prior to erasure was calculated using the equation:

$$Ed=SAL3\times 50/(SAL1\times 166,000) \qquad (2),$$

where the factor 50/166,000 corrects for the difference in dose in the measurements 1 and 3.

TABLE 1

Measured SAL values and calculated Ed values for MD-10 and CsBr:Eu$^{2+}$ screens

|      | MD-10 BaFBr:Eu$^{2+}$ | CsBr:Eu$^{2+}$ |
|------|-----------------------|-----------------|
| SAL1 | 440                   | 1,180           |
| SAL2 | 2,800                 |                 |
| SAL3 |                       | 290             |
| Ed   | 7.10−3                | 7.10−5          |

It is clear that CsBr:Eu has a much better erasability than the commercial BaFBr:Eu$^{2+}$ phosphor. As a consequence, much less erasure power is needed to erase the CsBr:Eu2$^+$ storage phosphor screen.

Hence, the object of the present invention can be accomplished by making an imaging system based on CsBr:Eu instead of BaFBr:Eu.

In a fourth measurement, the CsBr:Eu$^{2+}$ screen was homogeneously irradiated with a dose of ca. 185 R, also at 80 kVp.

Next, the screen was erased with the 500 Watt quartz-halogen lamp for 2 s. The light intensity on the screen was, again, 12 mW/cm$^2$.

After erasure, the screen was read out with the above-described scanner, and the SAL was determined. This measurement yielded the SAL4 value for the CsBr:Eu$^{2+}$ screen (Table 2).

Erasure depth, defined as the SAL after erasure divided by the SAL prior to erasure was calculated using the equation:

$$Ed = SAL4 \times 50/(SAL1 \times 185,000) \quad (2),$$

where the factor 50/185,000 corrects for the difference in dose in the measurements 1 and 4.

TABLE 2

Measured SAL values and calculated Ed value for the CsBr:Eu$^{2+}$ screen

|      | CsBr:Eu$^{2+}$ |
|------|----------------|
| SAL1 | 1,180          |
| SAL4 | 133            |
| Ed   | 3.10−5         |

Measurement 4 demonstrates that the required erasure depth can be achieved by erasing CsBr:Eu$^{2+}$ with an optical power of 12 mW/cm$^2$ in 2 s, which is equivalent to using an optical energy of 24 mJ/cm$^2$.

Calculation of the Required Electrical Power

A read out system is commonly designed for read out of phosphor screens having a variety of dimensions.

The largest screens that are used in medical radiography have a size of 35×43 cm$^2$, i.e. a size of 1,500 cm$^2$.

As indicated above, an erasure depth of 3.10$^{-5}$ is reached when the CsBr:Eu2+ screen is erased with an optical energy of 24 mJ/cm$^2$.

Incandescent lamps that are commonly used in erasure units, because they are available at high power, have an efficiency of ca. 5% in the transformation of electrical energy to light energy [Sristava, A M, T J Sommerer: Fluorescent Lamp Phosphors. The Electrochemical Society Interface, Summer 1998, p.28].

This implies that the calculated optical erasure energy corresponds to an electrical erasure energy of 480 mJ/cm$^2$.

It can be concluded that, to erase a CsBr:Eu$^{2+}$ storage phosphor screen in less than 0.5 s, as is desired to make a very high-throughput scanning system, an erasure unit is required with an electrical power of $S_{max} \times 1,000$ mJ, where $S_{max}$ is the surface area of the largest phosphor screen to be read in the read out apparatus.

A read out apparatus that allows to erase a phophor screen in 1 s is still a high throughput system and requires an erasure unit with an electrical power of $S_{max} \times 500$ mJ, where $S_{max}$ is the surface area of the largest phosphor screen to be read in the read out apparatus.

With an erasure unit having an electrical power of $S_{max} \times 250$ mJ a phosphor screen can be erased in 2 sec. It is generally accepted that even a system wherein 5 seconds are required to erase a phosphor screen is a relatively high throughput system. This kind of systems requires an erasing unit with an electrical power of $S_{max} 100$ mJ, wherein $S_{max}$ is the surface area of the largest hosphor screen read out in the readout apparatus.

It will be clear that lower power values are advantageous in that the heat produced by the erasing light source is less. However, a trade off has to be made between the lower amount of heat which is generated and the duration of the easing process which has to be selected so that the throughput of the system is not decreased to an unacceptable extent.

For some appllictions such as mammography and dental imaging very fast access is not needed. In these cases it is acceptable that the erasure process takes a bit more time. Hence, lower power but higher efficiency lamps like e.g. fluorescent lamps can be used for erasure.

Fluorescent lamps have an efficiency of about 40% in the transformation of electrical energy to light. [Sristava; A M, T J Sommerer: Fluorescent Lamp Phosphors. The Electrochemical Society Interface, Summer 1998, p.28]. This implies that the calculated optical erasure energy corresponds to an electrical erasure energy of 60 mJ/cm$^2$.

Although very fast image access is not required for the mentioned applications, it is still desirable to have the image within minutes.

Erasure of the phosphor screen should therefore preferably be possible within 2 minutes or 120 seconds.

A read out apparatus that allows to erase the storage phoshor screen in 120 seconds and having high efficiency lamps to erase, requires an erasure unit with an electrical power of $S_{max} \times 0.5$ mJ, where $S_{max}$ is the surface area of the largest phosphor screen to be read out in the readout apparatus.

It is even more desirable to erase the screen within 1 minute or 60 seconds. In this case the scanner requires an erasure unit with high efficiency lamps having an electrical power of $S_{max} \times 1$ mJ, where $S_{max}$ is the surface area of the largesst phosphor screen to be read out in the read out apparatus.

Optimally the screen is erased within 30 seconds, the erasure unit then requires an electrical power of $S_{max} \times 2$ mJ, where $S_{max}$ is the area of the largest phosphor screen to be read out in the readout apparatus.

What is claimed is:

1. Method of reading a radiation image that has been stored in a photostimulable phosphor screen having a surface area that is not greater than $S_{max}$ comprising the steps of (1) stimulating said phosphor screen by means of stimulating radiation, (2) detecting light emitted by the phosphor screen upon stimulation and converting the detected light into a signal representation of said radiation image, (3) erasing said phosphor screen by exposing it to erasing light, (4) said photostimulable phosphor screen comprises a divalent europium activated cesium halide phosphor wherein said halide is at least one of chloride and bromide obtained by the following steps:

mixing CsX with between $10^{-3}$ and 5 mol % of a Europium compound selected from the group consisting of $EuX'_2$, $EuX'_3$ and $EUOX'$, X' being a member selected from the group consisting of F, Cl, Br and I, firing the mixture at a temperature above 450° C., cooling said mixture, and recovering the CsX:Eu phosphor, and (5) said erasing light is emitted by an erasing light source assembly emitting in the wavelength range of 300 nm to 1500 nm and having an electrical erasing energy not greater than $S_{max} \times 1$ J.

2. A method according to claim 1 wherein said phosphor screen is obtained by the steps of preparing said CsX:Eu phosphor by firing a mixture of said CsX with between $10^{-3}$ and 5 mol % of an Europium compound selected from the group consisting of $EUX'_2$, $EUX'_3$ and $EuOX'$, X' being a halide selected from the group consisting of F, Cl, Sr and I and applying said phosphor on a substrate by a method selected from the group consisting of physical vapour deposition, thermal vapour deposition, chemical vapour deposition, radio frequency deposition and pulsed laser deposition.

3. A method according to claim 1 wherein said phosphor screen is obtained by the steps of bringing multiple containers of said CsX and an Europium compound selected from the group consisting of $EuX'_2$, $EuX'_3$ and $EuOX'$, X' being a halide selected from the group consisting of F, Cl, Br and I in condition for vapour deposition and depositing, by a method selected from the group consisting of physical vapour deposition, thermal vapour deposition, chemical vapour deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

4. A method according to claim 1 wherein said wavelength range is between 500 and 800 nm.

* * * * *

UNITED STATES PATENT AND TRADEMARK OFFICE
Certificate

Patent No. 6,504,169 B1

Patented: January 7, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul Leblans, Kontich, Belgium; Luc Struye, Mortsel, Belgium; Martin Devenney, Mountain View, CA; and Casper Reaves, San Jose, CA.

Signed and Sealed this Sixth Day of July 2004.

GEORGIA Y. EPPS
*Supervisory Patent Examiner*
Art Unit 2873